United States Patent [19]

Knifton

[11] Patent Number: 4,870,217
[45] Date of Patent: Sep. 26, 1989

[54] METHOD FOR PRODUCTION OF PHENOL/ACETONE FROM CUMENE HYDROPEROXIDE

[75] Inventor: John F. Knifton, Austin, Tex.

[73] Assignee: Texaco Chemical Company, White Plains, N.Y.

[21] Appl. No.: 261,818

[22] Filed: Oct. 24, 1988

[51] Int. Cl.$^4$ .................. C07C 37/08; C07C 45/53
[52] U.S. Cl. .................. 568/798; 568/485; 568/741; 568/768
[58] Field of Search .............. 568/741, 768, 298, 485

[56] References Cited

U.S. PATENT DOCUMENTS

| | | | |
|---|---|---|---|
| 2,628,984 | 2/1953 | Aller et al. | 568/798 |
| 2,715,145 | 8/1955 | Bawley et al. | 568/798 |
| 2,889,368 | 6/1959 | Hiratsuku et al. | 568/798 |
| 4,209,465 | 6/1980 | Austin et al. | 568/798 |
| 4,246,203 | 1/1981 | Wirth | 568/798 |
| 4,267,379 | 5/1981 | Austin | 568/798 |
| 4,267,380 | 5/1981 | Austin | 568/798 |
| 4,482,757 | 11/1984 | Drake | 568/798 |

FOREIGN PATENT DOCUMENTS

| | | | |
|---|---|---|---|
| 0157531 | 12/1979 | Japan | 568/798 |
| 0992508 | 1/1983 | U.S.S.R. | 568/798 |

*Primary Examiner*—Werren B. Lone
*Attorney, Agent, or Firm*—Jack H. Park; Kenneth R. Priem; Cynthia L. Kendrick

[57] ABSTRACT

A method is disclosed for the synthesis of phenol and acetone by acid-catalyzed decomposition over a catalyst comprising an acidic smectite clay, particularly an acidic montmorillonite silica-alumina clay. The method allows for quantitative conversions with yields of up to 98% mole or better. Further the method is capable of operating efficiently at high LHSVs.

17 Claims, No Drawings

METHOD FOR PRODUCTION OF PHENOL/ACETONE FROM CUMENE HYDROPEROXIDE

CROSS-REFERENCE

This application is related to U.S. patent application Ser. Nos. 261,817 and 261,819.

This invention relates to improvements in methods for decomposition of organic hydroperoxides, and more particularly this invention relates to a method for producing phenol and acetone by decomposition of cumene hydroperoxide over a smectite clay catalyst. Particularly effective smectite clays are the montmorillonite silica-alumina clays. The invention is particularly advantageous in that the decomposition takes place at mild temperatures, phenol is generated in at least as high as 98% mole yield, the catalyst is very attractive in that it is relatively inexpensive, and by-products are produced in a much smaller percentage than with standard acid catalysis.

BACKGROUND OF THE INVENTION

It is known to those skilled in the art that cumene can be oxidized to cumene hydroperoxide and that cumene hydroperoxide can be decomposed by various means to provide phenol and acetone.

In U.S. Pat. No. 2,889,368 to Hiratsuka there is a process discussed for the decomposition of various organic hydroperoxide substances, such as, for example, cumene hydroperoxide. The cumene hydroperoxide is decomposed in the presence of a 10 to 70% aqueous sulfuric acid solution at a temperature between about 50° and 100° C. to phenol and acetone, the yields amounting to 80-90%.

Today, the disadvantages of using soluble strong acid catalysts in this application include (a) the need for an efficient means of separating the phenol/acetone products from the acid or spent acid catalyst, (b) the need to neutralize said acids with caustic etc., (c) the disposal of salts generated as a result of said neutralization, and (d) the difficulty in obtaining >99.9% purity phenol from such a process if there is any entrainment or contamination of the crude phenol/acetone product by said acid catalyst.

U.S. Pat. No. 2,715,145 concerns a process for increasing the yield of phenol by decomposing the material contained in the peroxide acidic catalyst decomposition mixture. Again it is disclosed that the decomposition can be promoted by the addition to the residue of acids such as sulphuric acid, phosphoric acid or sulphonic acids, as well as acid washed activated earth, such as fuller's earth.

A decomposition catalyst of sulfur dioxide or sulfuric acid is also used in U.S. Pat. No. 4,016,213 to obtain phenol and acetone from cumene hydroperoxide.

In U.S. Pat. No. 4,246,203 a hydroperoxide of an aromatic compound is converted to a volatile phenol and a carbonyl compound in a cleavage decomposition reaction. Here a wide range of both solid and liquid cleavage catalysts may be used including acetic acid, sulphur dioxide, sulphur, formic acid, phosphoric acid and fluoroboric acid, although sulfuric acid is preferred. Silica/alumina gave rather poor yields of phenol and acetone under these conditions.

Lewis acid catalysts were employed in the invention of U.S. Pat. No. 4,267,380, to Austin et al., to decompose cumene hydroperoxide to phenol and acetone. Some Lewis acids were unsatisfactory or, in some cases, found to be catalytically inert. Preferred Lewis acids were tungsten hexafluoride, silicon tetrafluoride, stannous chloride, stannic fluoride, antimony pentachloride, sulfur monochloride and sulfur tetrafluoride.

In U.S. Pat. No. 4,209,465, also to Austin et al., it was found that cumene hydroperoxide could be decomposed to phenol and acetone using an isolable carbonium, tropylium or oxonium salt, such as triphenylcarbonium tetrafluoroborate, as the catalyst.

In another patent to Austin et al., U.S. Pat. No. 4,267,379, cumene hydroperoxide is decomposed to phenol and acetone using boron trifluoride or boron trifluoride complexed with an oxygen-containing polar compound.

In U.S. Pat. No. 4,358,618 there is described a process for decomposing a cumene oxidation product mixture by mixing the product with an acid that lowers the cumene hydroperoxide concentration and converts most of the dimethylphenol carbinol to dicumyl peroxide.

In an article by Augustin et al, in *Stud. Univ. Babes-Bolyai, Chem.* 1986, 31, 19–23 (see Chem. Abstracts 107: 236170j, 1987), the life of synthetic aluminosilicate catalysts in the decomposition of cumene hydroperoxide was studied.

In U.S. Pat. No. 4,743,573 to Romano there was described catalysts for the selective decomposition of cumene hydroperoxide into phenol and acetone which comprise oxide forms of silicon, aluminum and boron in the form of crystals having a structure of zeolite wherein aluminum and boron replace silicon in the crystalline structure of silica and wherein the crystals are interconnected by oligomeric silica. The phenol selectivity is typically 80.5 to 96% with these catalyts in batch studies, and higher than 98% in continuous synthesis at cumene hydroperoxide conversion levels of 90%.

European patent application No. 203-632-A describes a catalyst for decomposition of cumene hydroperoxide to produce phenol and acetone comprising zeolite crystals containing boron and aluminum bonded with silica. A portion of the silicon atoms in the crystal lattice of silica are replaced by Al and B and the zeolite crystals are bonded to each other by a siliceous bonding agent which allows the catalyst to assume the shape of mechanically stable microspheres.

Carboxylic acid derivatives have also been used to catalyze cumene hydroperoxide decomposition. See *Izv. Akad. Nauk Turkm.* 5512, Ser. Fiz.—Tekh, Khim, Geol. Nauk 1987, (2), 108–10 (Russ) and Chem. Abstracts 108: 55583w (1988).

Molybdenum, vanadium and titanium catalysts have also been used for the catalytic decomposition of cumyl hydroperoxide to yield mainly phenol and acetone. See Stozhkova, G. A., et al. (Yarosl. Politekh. Inst., Yaroslavl, USSR) *Neftekhimiya* 1987, 27(1), 137–41 (Russ) and Chem. Abstracts 107: 197676g (1987).

In an article titled "Catalysis: Selective Developments", *Chem. Systems Report* 84-3, 239–249, at Section 3.4320, the unusual properties of smectite clays which make them of interest as catalysts are discussed. These compositions are layered and exhibit a 2:1 relationship between tetrahedral and octahedral sites. In addition, the combination of cation exchange, intercalation and the fact that the distance between layers can be adjusted provide interesting possibilities.

There is a discussion of clay mineral catalysts, including "acid" montmorillonite clay catalysts in "Progress in Inorganic Chemistry", Vol. 35, p. 41 (1987). The process of pillaring this type of catalyst is discussed. Pillaring can convert a clay lamellar solid into a more heat resistant two dimensional zeolite material.

In the cases where acidic substances are utilized as the catalysts the yields are satisfactory, however many of these acid catalysts require substantial expenditure for production of phenol and acetone, there are disposal problems with spent acids or their salts, and there are difficulties in achieving >99.9% purity phenol required by today's market place due to entrainment or breakthrough of said acids. In addition, by-products such as mesityl oxide, α-methylstyrene, acetophenone and 2-phenyl-2-propanol are produced along with the product and must somehow be removed and processed.

It would be a substantial advance in the art if phenol and acetone could be produced in yields approaching 100% by decomposition over an inexpensive heterogeneous catalyst using mild conditions. A catalyst which worked at very high space velocities using mild conditions and yet afforded high selectivities and yields with a smaller percentage of by-products would be particularly advantageous. Furthermore a very active, long life heterogeneous catalyst would also solve the catalyst disposal and acid entrainment problems cited above.

SUMMARY OF THE INVENTION

In accordance with certain of its aspects, the novel method of this invention for continuous cogeneration of phenol and acetone comprises reacting cumene hydroperoxide in the presence of a catalyst comprising a smectite clay, or particularly a montmorillonite silica-alumina clay, at mild temperature and pressure. Examples demonstrate the effectiveness of montmorillonite clays in powdered and extrudated form under mild conditions.

A particular advantage of the instant invention over the prior art is that it has been discovered in the instant invention that smectite clays, especially montmorillonite silica-alumina clays have properties which allow for distinct improvements over the use of ordinary silica and alumina catalysts. The method of the instant invention allows for quantitative conversions with yields of up to 98 mole% or better. In addition, LHSVs of 60 or greater have also been demonstrated.

DESCRIPTION OF THE INVENTION

Preparation of the product of this invention may be carried out typically by reacting cumene hydroperoxide in the presence of a decomposition catalyst comprising smectite clay. The decomposition is carried out continuously and the catalyst preferably comprises a montmorillonite silica-alumina clay in powdered, granular or extruded form.

The reaction can be represented by the following:

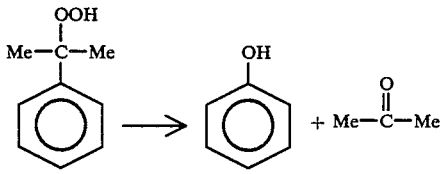

The same method may also be applied to the reaction of other hydroperoxides. For example, the proces may be applied to the decomposition of aromatic hydroperoxides such as sec-butylbenzene hydroperoxide, ethylbenzene hydroperoxide and cyclohexylbenzene hydroperoxide.

The catalysts used to effect this reaction are preferably silica and alumina-rich montmorillonite clay catalysts. The catalysts are effective in the form of powders, granules or extrudates.

A variety of clay catalysts containing aluminum and silica are effective in the subject reaction (Eq. 1), however it is necessary that the alumina or silica be acidic under normal operating conditions. As discussed, a group of catalysts which works well in this synthesis are acidic clay mineral catalysts. Chemically clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in the reaction of Equation 1 are smectite clays. Smectite clays are discussed in the article cited in Chem. Systems Report, 84-3. These clays have small particle size and unusual intercalation properties which afford them high surface area. They are alumino silicates with a unique structure that permits modifications which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. What renders the smectites of particular interest among the clay minerals is their combination of cation exchange, intercalation and swelling properties.

The three-layer sheet types of smectite clays include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure is:

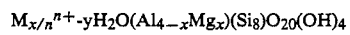

where M represents the interlamellar (balancing cation, normally sodium or lithium and x, y and n are integers.

These montmorillonite clays are best used in the present application in an acidic form. Acids activate montmorillonites by attacking and solubilizing structural cations in the octahedral layers. This opens up the clay structure and increases surface area. These acid treated clays act as strong Bronsted acids.

Acidic montmorillonite clays are the preferred form of smectite clay in the present invention. Preferably these acid clays should have acidities in the range of 3 to 15, or greater, mg KOH/gm, titrated to a phenolphthalein end point. Their surface area should be >30 m²/g, and preferably 200 to 1000 m²/g. Their moisture content should be limited also, thereby upon heating to 220° F., the weight loss is generally less than 20 wt%.

Illustrative examples of suitable montmorillonite clays include powdered clays such Filtrol Grade 13, 113 and 160, sold by Harshaw-Filtrol, clays in granular form, such as filtrol grade 24, having a 20-60 mesh size, and grade 25 (10/20 mesh) sold by Harshaw-Filtrol, as well as extruded clays such as the Filtrol Clay-62, sold in 1/16" and 3/16" diameter extrudates.

Hydroperoxide decomposition may be conducted batchwise, in a continuous slurry bed reactor, or in a fixed-bed, continuous flow, reactor. For practical reasons a fixed bed process is preferred. In all cases the catalyst concentration should be sufficient to provide the desired catalytic effect.

Cogeneration of phenol and acetone can generally be conducted at temperatures from 20° to 150° C.; the preferred range is 40° to 120° C. The operating pressure may be from zero to 1000 psig, or higher. The preferred pressure range is 100 to 400 psig. Because of the highly exothermic nature (52 kal/mole) of the cumene hydroperoxide decomposition (Eq. 1), temperature control is particularly important, especially in a fixed catalyst bed process.

Typically, phenol is generated continuously in up to ca. 50 wt% concentration in the crude product liquid effluent, and likewise, acetone may be generated in 30-50 wt% concentrations. The cumene hydroperoxide should preferably be as pure as possible, but an 80% purity is certainly acceptable. Typical impurities in such an "80%" cumene hydroperoxide feed are cumene, 2-phenyl-2-propanol and acetophenone. Said cumene hydroperoxide is generally diluted with inert solvent, or product, prior to being fed to the decomposer. Typical diluents include acetone, or a mix of acetone, cumene and phenol.

Generally cumene hydroperoxide conversions are quantitative in continuous unit operations. Phenol yields, based on hydroperoxide charged, are many times 98 mole% or better. Likewise, acetone yields are also 98 mole% or better.

These yields are achieved at total liquid hourly space velocities (LHSV) of one to 10 under mild conditions. LHSVs of 60, or greater, have also been demonstrated to be useful in achieving quantitative cumene hydroperoxide conversion.

Here LHSV is defined as follows:

$$LHSV = \frac{\text{Weight Of Total Liquid Feed Run Through The Reactor Per Hour}}{\text{Volume of Catalyst In Reactor}}$$

The examples which follow illustrate the cogeneration of phenol and acetone from cumene hydroperoxide using clay mineral catalysts, particularly montmorillonite clay catalysts. The examples are only intended as a means of illustration and it should be understood that the invention is not meant to be limited thereby.

Conversion of cumene hydroperoxide (wt%) is estimated in the following examples using the equation:

$$\frac{[\text{Wt \% Conc. of } (C_6H_5C(CH_3)_2OOH \text{ in Feed} - \text{Wt \% Conc. of Cumene Hydroperoxide in product}]}{\text{Wt \% Conc. of Cumene Hydroperoxide in Feed}} \times 100$$

Yields of phenol/acetone ($C_6H_5OH/CH_3COCH_3$, mole%) are estimated from:

$$\frac{\text{Moles of Phenyl or Acetone in Product Liquid}}{\text{Moles of Cumene Hydroperoxide in feed}} \times 100$$

EXAMPLE 1

The data in Example 1 illustrates the quantitative conversion of cumene hydroperoxide to phenol/acetone catalyzed by Harshaw-Filtrol Clay-24, an acidic montmorillonile clay in granular form. The reaction is conducted under mild conditions. Minor by-products include alpha-methylstyrene, however they are present in much smaller amounts than in the related art; cumene, acetophenone and 2-phenyl-2-propanol are present in the cumene hydroperoxide feed and apparently these by-products remain to some extent in the mix during peroxide decomposition.

A 250-ml round bottom flask fitted with a condenser, heater, stirrer and feed control was charged with a mixture of 60.0 g of acetone and 5.0 g of Harshaw-Filtrol Clay-24 (acidity 8.5 mg KOH/gm, surface area 425 m²/g), in granular form. The mixture was heated to reflux (57° C.) with stirring, and 40.0 g of "80%" cumene hydroperoxide solution[a] added dropwise at a rate such that the pot temperature did not exceed 80° C. After the peroxide addition was complete, the mixture was heated to reflux for an additional 2 hours.

Upon cooling, the product mix was weighed (104.0 g) and the product (volume 110 cc) neutralized with sodium bicarbonate and analyzed by glc.

| Analysis showed the following composition (wt %): | |
|---|---|
| Acetone | 69.8 |
| Phenol | 19.4 |
| Cumene | 6.9 |
| Alpha-methyl styrene | 2.3 |
| 2-phenyl-2-propanol | 0.4 |
| Acetophenone | 0.4 |
| Cumene hydroperoxide | <0.1 |
| Feed Composition: | |
| Cumene hydroperoxide | 78.5 |
| Cumene | 16.5 |
| 2-phenyl-2-propanol | 4.7 |
| Acetophenone | 0.4 |

From these data it may be noted that:

(a) The estimated yield of phenol (based on cumyl hydroperoxide charged is: 98 mole%.

(b) A substantial portion of the 2-phenyl-2-propanol in the feed is also converted to product.

(c) There is no significant quantity of mesityl oxide by-product formed with this catalyst.

(d) Cumene hydroperoxide conversion is essentially quantitative.

EXAMPLE 2-5

Table 1 illustrates the generation of phenol/acetone in batch equipment under the same mild conditions of Example 1, but using a variety of other acidic montmorillonite clays. These clays vary in acidity from 3.0 to 15 mg KOH/gm and are in powder and extruded form.

TABLE I

PHENOL/ACETONE FROM CUMENE HYDROPEROXIDE[a]

| | | Product Composition (Wt %) | | | | | | |
|---|---|---|---|---|---|---|---|---|
| Ex. | Catalyst | Acetone | Cumene | α-Methyl Styrene | Phenol | 2-phenyl-2-Propanol | Acetophenone | Cumene Hydroperoxide |
| 2 | Clay-113b | 72.3 | 6.8 | 1.8 | 18.7 | 0.1 | 0.2 | — |

TABLE I-continued

PHENOL/ACETONE FROM CUMENE HYDROPEROXIDE[a]

| | | Product Composition (Wt %) | | | | | | |
|---|---|---|---|---|---|---|---|---|
| Ex. | Catalyst | Acetone | Cumene | α-Methyl Styrene | Phenol | 2-phenyl-2-Propanol | Aceto-phenone | Cumene Hydro-peroxide |
| 3 | Clay-13c | 70.0 | 7.3 | 1.3 | 20.1 | 1.0 | 0.3 | — |
| 4 | Clay-160d | 69.4 | 7.2 | 0.3 | 20.8 | 1.7 | 0.3 | 0.2 |
| 5 | Clay-62e | 63.4 | 7.2 | 0.3 | 7.3 | 2.0 | 0.2 | 19.5 |

[a] Run in Batch, Glassware Equipment as in Example 1.
[b] Powder, 10 mg KOH/mg Acidity, Surface Area 300 m²/g, from Harshaw-Filtrol.
[c] Powder, 15 mg KOH/gm Acidity, Surface Area 300 m²/g, from Harshaw-Filtrol.
[d] Powder, 13 mg KOH/gm Acidity, Surface Area 330 m²/g, from Harshaw-Filtrol.
[e] Extrudate, 3/16″ Diameter, 3.0 mg KOH/gm Acidity, Surface Area 275 m²/g, from Harshaw-Filtrol.

EXAMPLES 6 AND 7

This example illustrates the generation of phenol/acetone in continuous unit equipment using the Harshaw-Filtrol Clay-24 catalyst.

A 200 cc plug-flow reactor, equipped with Dow-Therm cooling capabilities, heating, pressure and flow controls, was charged with 150 cc of Clay-24 catalyst. The catalyst bed was first pretreated with acetone at 60° C., then a mix of "80%" cumene hydroperoxide (CHP of composition shown in Example 1), diluted to 20% concentration with >99% grade acetone, was fed upflow, at two flow rates (150 and 600 cc/hr) at a reactor temperature of 60° C. and 300 psi pressure. The crude liquid product was collected and analyzed. Results are summarized in Table II.

It is considered significant here that in these runs:

(a) The cumene hydroperoxide conversion is quantitative over this range of conditions.

(b) Acetophenone, 2-phenyl-2-propanol, mesityl oxide and α-methylstyrene concentrations in the crude product are all low.

Due to the exothermic nature of the cumene hydroperoxide decomposition reaction (52 Kcal/mol), the temperature profile along the catalyst bed in these runs typically ranged from 60°-100° C. at the beginning of the run, down to 60°-83° C. under equilibrium conditions.

EXAMPLE 8

This example illustrates the generation of phenol/acetone in continuous unit equipment using the Clay-24 catalyst and a cumene hydroperoxide feedstock diluted with acetone/cumene/phenol mix.

Employing the reactor and procedures of Example 6, 150 cc of Clay-24 were pretreated with acetone (150 cc/hr) at 60° C., then fed a mixture of "80%" cumene hydroperioxide (900 g, composition as in Example 1) diluted with acetone/cumene/phenol (6.4:2.4:9.2 weight ratio, 2100 g) at a feed rate of 150 cc/hr. Operating temperatures and pressures were 60° C. and 300 psi. Samples of crude liquid product effluent were collected and analyzed. Results are summarized in Table III.

It may be noted that in typical samples, e.g. Sample #8:

Estimated Phenol Yield = >99 mole %
Estimated Acetone yield = 97 mole %

No significant quantity of mesityl oxide was found in the crude product.

Cumene hydroperoxide conversion is quantitative.

A significant portion of the 2-phenyl-2-propanol in the liquid feed is also converted to products.

Material balance data are consistently >99%, and typically 99.3+%.

Due to the exothermic nature of the peroxide decompositon reaction, the temperature profile along reactor bed in this run varied from 60°-93° C. at the onset to 60°-73° C. under equilibrium conditions.

TABLE II

PHENOL/ACETONE FROM CUMENE HYDROPEROXIDE[a,b]

| | | | | | Crude Product Composition (Wt %) | | | | | | | |
|---|---|---|---|---|---|---|---|---|---|---|---|---|
| Ex. | Temp. (C°)a | Press (psi) | Feed Rate (g/hr) | Sample | Acetone | Mesityl Oxide | Cumene | Phenol | α-methyl Styrene | Aceto-Phenone | 2-Phenyl 2-Propanol | Cumene Hydro-peroxide |
| 6 | 60 | 300 | 150 | 2 | 78.7 | 0.3 | 4.3 | 14.3 | 1.4 | 0.5 | 0.1 | — |
| | | | | 6 | 79.1 | 0.1 | 4.3 | 14.3 | 1.5 | 0.4 | 0.1 | — |
| | | | | 8 | 79.5 | 0.2 | 3.7 | 14.7 | 1.4 | 0.3 | — | — |
| | | | | 10 | 79.9 | 0.2 | 3.6 | 14.3 | 1.4 | 0.3 | — | — |
| | | | | 14 | 79.7 | 0.2 | 3.7 | 14.4 | 1.5 | 0.2 | — | — |
| | | | | 18 | 79.6 | 0.1 | 3.7 | 14.7 | 1.4 | 0.2 | — | — |
| 7 | 60 | 300 | 600 | 1 | 79.8 | 0.2 | 3.6 | 14.4 | 1.3 | 0.3 | — | — |
| | | | | 5 | 80.4 | 0.1 | 3.6 | 14.0 | 1.4 | 0.2 | — | — |
| | | | | 6 | 80.2 | 0.1 | 3.6 | 14.3 | 1.3 | 0.2 | — | — |
| | | | | 10 | 80.3 | 0.1 | 3.6 | 14.2 | 1.4 | 0.2 | — | — |

[a] Run in continuous, Dowtherm jacketed reactor, upflow, with 150 cc of catalyst charge.
[b] Catalyst: Harshaw-Filtrol Clay-24, granules (Acitiy 8.5 mg KOH/gm, Surface Area 425 m²/g).

TABLE III

PHENOL/ACETONE FROM CUMENE HYDROPEROXIDE

Crude Product Composition (Wt %)

| Ex. | Catalyst | Temp. °C. | Feed Rate (g/hr) | Sample | Acetone | Mesityl Oxide | Cumene | Phenol | Methyl Styrene | Aceto Phenone | 2-phenyl 2-Propanol | Cumene Hydro- peroxide | 4-Cumyl Phenol |
|---|---|---|---|---|---|---|---|---|---|---|---|---|---|
| 8 | Clay-24[a] | 60 | 150 | 2 | 33.1 | — | 14.0 | 50.6 | 0.4 | — | 0.3 | — | 1.0 |
| | | | | 3 | 26.8 | — | 14.8 | 55.8 | 0.4 | 0.3 | — | — | 1.1 |
| | | | | 4 | 25.3 | — | 15.0 | 57.1 | 0.3 | 0.3 | — | — | 1.2 |
| | | | | 7 | 25.9 | — | 15.1 | 56.8 | 0.3 | 0.3 | — | — | 0.9 |
| | | | | 8 | 32.9 | — | 14.0 | 51.2 | 0.3 | 0.2 | — | — | 0.7 |
| | | | | 11 | 32.0 | — | 14.2 | 51.9 | 0.3 | — | 0.2 | — | 0.9 |
| | | | | 12 | 31.1 | — | 14.2 | 52.6 | 0.3 | — | 0.2 | — | 0.9 |
| | | | | 15 | 32.7 | — | 14.0 | 51.5 | 0.3 | — | 0.2 | — | 0.6 |
| | | | | 16 | 33.2 | — | 13.9 | 50.7 | 0.4 | 0.3 | — | — | 0.7 |
| | | | | 17 | 33.2 | — | 14.1 | 50.7 | 0.4 | 0.2 | — | — | 0.8 |
| | | | | 20 | 33.2 | — | 14.1 | 50.7 | 0.4 | 0.2 | — | — | 0.8 |
| | | | | 22 | 33.3 | — | 14.0 | 50.8 | 0.4 | 0.2 | — | — | 0.7 |
| Feed: | | | | | 24.3 | | 13.8 | 36.6 | | 0.1 | 1.4 | 23.2 | 0.1 |

[a]Harshaw-Filtrol Clay-24, Granules

EXAMPLE 9

This example illustrates the generation of phenol/acetone at higher feed rates, up to a LHSV=10.

Using the reactor and procedures of Example 6 and a feed composition similar to that of Example 8, a fresh sample of Clay-24 catalyst was evaluated at a series of different feed rates (i.e. 0.99, 1.65 and 3.3 lb/hr, corresponding to liquid hourly space velocities LHSVs, of 3.0, 5.0 and 10.0 respectively).

Results are summarized in Table IV.

It may be noted that in typical samples, e.g. Sample #17:

Estimated Phenol Yield=98 mole %
Estimated Acetone yield=>99 mole %

Cumene hydroperoxide conversion is essentially quantitative even at high LHSVs of ten.

The temperature profile along the reactor bed typically varied in this run from 60°–107° C. at LHSVs of 3, to 81°–105° C. at LHSVs of 10.

TABLE IV

PHENOL/ACETONE FROM CUMENE HYDROPEROXIDE[b]

Product Composition (Wt %)

| Ex. | Catalyst | Temp. °C. | Feed Rate (g/hr) | Sample | Acetone | Mesityl Oxide | Cumene | Phenol | Methyl Styrene | Aceto Phenone | 2-phenyl 2-Propanol | Cumene Hydro- peroxide | 4-Cumyl Phenol |
|---|---|---|---|---|---|---|---|---|---|---|---|---|---|
| 9 | Clay-24[a] | 60 | 0.99 | 1 | 33.4 | — | 14.2 | 50.4 | 0.9 | — | 0.3 | — | 0.3 |
| | | | | 3 | 33.4 | — | 14.1 | 50.3 | 1.0 | — | 0.3 | — | 0.2 |
| | | | | 6 | 33.4 | — | 14.1 | 50.5 | 0.9 | — | 0.2 | — | 0.3 |
| | | | 1.65 | 7 | 33.5 | — | 14.1 | 50.3 | 1.0 | — | 0.3 | — | 0.2 |
| | | | | 9 | 33.5 | — | 14.1 | 50.4 | 1.1 | — | 0.2 | — | 0.2 |
| | | | | 12 | 33.4 | — | 14.0 | 50.9 | 0.9 | — | 0.2 | — | 0.1 |
| | | | 3.3 | 13 | 33.5 | — | 14.1 | 50.6 | 1.0 | — | 0.3 | 0.1 | 0.3 |
| | | | | 14 | 33.3 | — | 14.1 | 50.7 | 1.0 | — | 0.3 | — | 0.1 |
| | | | | 17 | 33.3 | — | 14.1 | 50.8 | 1.0 | — | 0.2 | — | 0.2 |
| Feed: | | | | | 24.4 | | 14.1 | 37.2 | | 0.1 | 1.5 | 22.7 | |

[a]Harshaw-Filtrol, Clay, Grade-24

EXAMPLE 10

This example illustrates the longevity of the Clay-24 catalyst when used in phenol/acetone production service.

A 50 cc capacity, plug flow, electrically heated reactor equipped with pressure and flow controls, was charged with 25 cc of Clay-24 catalyst. A liquid mix of 80% cumene hydroperoxide diluted with acetone/cumene/phenol (6.4:2.4:9.2 weight ratio) was pumped through the catalyst bed for a total of 43 days. Operating conditions were 60° C., 300 psi, 25 cc/hr feed rate.

A summary of the results in Table V, shows that catalyst activity remains good over the 43 day (1000+ hr) run period, with no need for catalyst regeneration or replacement.

TABLE V

PHENOL/ACETONE FROM CUMENE HYDROPEROXIDE

Product Composition (Wt %)

| Ex. | Catalyst | Sample | Acetone | Mesityl Oxide | Cumene | Phenol | Methyl Styrene | Aceto Phenone | 2-Phenyl 2-Propanol | Cumene Hydro- peroxide | 4-Cumyl Phenol | Time (Days) |
|---|---|---|---|---|---|---|---|---|---|---|---|---|
| 10 | Clay-24 | 1 | 33.6 | — | 14.1 | 49.8 | 1.5 | 0.2 | 0.1 | 0.1 | — | 1 |
| | | 2 | 33.4 | — | 14.5 | 50.0 | 0.6 | 0.2 | — | — | 0.8 | 10 |
| | | 3 | 33.5 | — | 14.4 | 49.9 | 0.6 | 0.2 | 0.1 | 0.2 | 0.6 | 22 |
| | | 4 | 33.4 | — | 14.4 | 49.9 | 0.6 | 0.2 | 0.1 | 0.4 | 0.5 | 29 |
| | | 5 | 34.0 | — | 11.9 | 50.2 | 0.8 | 0.4 | 0.4 | 1.4 | 0.5 | 38 |
| | | 6 | 33.3 | — | 13.8 | 50.0 | 0.7 | 0.2 | 0.2 | 1.1 | 0.4 | 43 |

TABLE V-continued

PHENOL/ACETONE FROM CUMENE HYDROPEROXIDE

| | | | | Product Composition (Wt %) | | | | | | | | |
|---|---|---|---|---|---|---|---|---|---|---|---|---|
| Ex. | Catalyst | Sample | Acetone | Mesityl Oxide | Cumene | Phenol | Methyl Styrene | Aceto Phenone | 2-Phenyl 2-Propanol | Cumene Hydro- peroxide | 4-Cumyl Phenol | Time (Days) |
| | Feed: | | 24.8 | | 14.7 | 35.7 | — | 0.1 | 1.4 | 23.2 | | |

EXAMPLE 11

This example illustrates the generation of phenol-/acetone at LHSVs up to 60.

The 200 cc capacity, upflow reactor of Example 6 was charged with a 25 cc plug (3-4 ins long) of Clay-24 catalyst. After pretreatment with acetone, the reactor was fed a mix of 80% cumene hydroperoxide diluted with acetone/cumene/phenol, as in Example 8, but to a CHP level of only 1.5 wt%. The liquid feed rate was 3.3 lb/hr, the effective LHSV was ca. 60.

Samples of product effluent were analyzed periodically.

Cumene hydroperoxide conversion was essentially quantitative, see Table VI. Phenol and acetone concentration rose measurably.

range 100 to 1000 psi. The results are summarized in Table VII.

Of Note:

(a) Cumene hydroperoxide conversion was quantitative over the full range of conditions, even though high feed throughputs were employed.

(b) At 50° C. operating temperature (Example 12, Sample #3):
Phenol Yield=97 mole%
Acetone Yield=99 mole %

(c) At 80° C. operating temperature (Example 14, Sample #3):
Phenol Yield=94 mole%
Acetone Yield=>99 mole%

(d) At 100 psi operating pressure (Example 15, Sample #3)
Phenol Yield=95 mole%
Acetone Yield=97 mole%

TABLE VI

PHENOL/ACETONE FROM CUMENE HYDROPEROXIDE

| | | | | Product Composition | | | |
|---|---|---|---|---|---|---|---|
| Ex. | Catalyst | Temp (°C.) | Feed Rate (lb/hr) | Sample | Acetone | Cumene | Phenol | Cumene Hydroperoxide |
| 11 | Clay-24 | 60 | 3.3 | 1 | 35.2 | 13.9 | 50.7 | — |
| | | | | 3 | 34.9 | 13.9 | 51.0 | — |
| | Feed: | | | | 34.6 | 13.9 | 49.8 | 1.5 |

EXAMPLE 12-16

TABLE VII

PHENOL/ACETONE FROM CUMENE HYDROPEROXIDE

| Ex. | Catalyst | Pressure (psi) | Temp (°C.) | Feed Rate (lb/hr) | Sample | Acetone | Methyl Oxide | Cumene | Phenol | Methyl Styrene | Aceto Phenone | 2-Phenyl 2-Propanol | Cumene Hydro- Peroxide | 4-Cumene Phenol |
|---|---|---|---|---|---|---|---|---|---|---|---|---|---|---|
| 12 | Clay-24 | 300 | 50 | 3.3 | 1 | 33.8 | — | 13.8 | 49.9 | 0.9 | 0.3 | — | — | 0.8 |
| | | | | | 2 | 31.0 | — | 14.1 | 52.5 | 0.9 | 0.3 | — | — | 0.8 |
| | | | | | 3 | 33.9 | — | 13.7 | 50.2 | 0.8 | 0.3 | — | — | 0.7 |
| 13 | Clay-24 | 300 | 48 | 3.3 | 4 | 34.3 | — | 13.7 | 49.6 | 0.8 | 0.2 | — | — | 0.6 |
| | | | | | 5 | 31.3 | — | 14.0 | 52.2 | 0.9 | 0.3 | — | — | 0.6 |
| | | | | | 6 | 34.1 | — | 13.6 | 50.0 | 0.8 | 0.2 | — | — | 0.6 |
| 14 | Clay-24 | 300 | 80 | 3.3 | 1 | 34.1 | — | 13.8 | 49.6 | 1.0 | 0.3 | — | — | 0.7 |
| | | | | | 2 | 31.3 | — | 14.2 | 51.8 | 1.0 | 0.3 | — | — | 0.8 |
| | | | | | 3 | 34.2 | — | 13.8 | 49.5 | 0.9 | 0.3 | — | — | 0.7 |
| 15 | Clay-24 | 100 | 60 | 3.3 | 1 | 34.0 | — | 13.8 | 49.8 | 0.9 | 0.3 | — | — | 0.6 |
| | | | | | 2 | 30.3 | — | 14.3 | 52.8 | 0.9 | 0.3 | — | — | 0.6 |
| | | | | | 3 | 33.8 | — | 13.8 | 49.9 | 0.9 | 0.3 | — | — | 0.6 |
| 16 | Clay-24 | 1000 | 60 | 3.3 | 4 | 34.1 | — | 13.7 | 49.7 | 0.8 | 0.3 | — | — | 0.6 |
| | | | | | 5 | 29.9 | — | 14.3 | 53.2 | 0.9 | 0.3 | — | — | 0.6 |
| | | | | | 6 | 34.1 | — | 13.7 | 49.8 | 0.9 | 0.3 | — | — | 0.6 |
| | Feed: | | | | | 24.6 | — | 13.7 | 35.7 | — | 0.1 | 1.6 | 23.9 | — |
| | | | | | | 24.7 | — | 13.8 | 35.5 | — | 0.2 | 1.5 | 24.0 | — |
| | | | | | | 24.6 | — | 13.6 | 35.2 | — | 0.1 | 1.6 | 24.5 | — |
| | | | | | | 24.9 | — | 13.7 | 35.7 | — | 0.1 | 1.6 | 24.0 | — |

These examples illustrate the syntheses of phenol and acetone using Clay-24 catalyst over a range of temperatures and pressures.

Following the procedure of Example 6, the Clay-24 catalyst was tested using the "80%" cumene hydroperoxide feed in acetone/cumene/phenol over the temperature range of 48°-80° C. and the operating pressure

EXAMPLE 17

This example illustrates the use of an extruded clay catalyst in continuous acetone/phenol service.

Following the procedures of Example 6, the reactor was charged with 150 cc of Harshaw-Filtrol Clay-62, 1/6" diameter extrudates. The typical feed, "80%" cumene hydroperoxide diluted with acetone/cumene/phenol, was pumped through the bed at a reactor temperature of 80° C. and flow rates of between 3 and 10 LHSV. Analyses of effluent samples are summarized in Table VIII.

It may be noted that:
(a) Cumene hydroperoxides are typical 96-100% per pass.
(b) For Sample #7
Phenol Yield=94 mole%
Acetone Yield=>99 mole%

At the LHSV of 3, the temperature profile along the reactor bed was typically 80°-108° C.; at LHSV=10, the typical range was up to 118° C.

TABLE VIII

| | | | | | | ACETONE/PHENOL FROM CUMENE HYDROPEROXIDE | | | | | | |
|---|---|---|---|---|---|---|---|---|---|---|---|---|
| | | | | | | Product Composition (Wt %) | | | | | | |
| Ex. | Catalyst | Pressure (psi) | Temp. °C. | Feed Rate (lb/hr) | Sample | Acetone | Mesityl Oxide | Cumene | Phenol | Methyl Styrene | Aceto Phenone | 2-phenyl 2-Propanol | Hydroperoxide | Cumene 4-Cumyl Phenol |
| 17 | Clay-62 1/16" | | | | | | | | | | | | | |
| | | 300 | 80 | 0.99 | 1 | 28.6 | — | 14.2 | 54.7 | 1.0 | 0.3 | 0.1 | — | 0.6 |
| | | | | | 2 | 34.5 | — | 13.6 | 49.5 | 0.9 | 0.2 | 0.1 | — | 0.6 |
| | | | | | 3 | 34.0 | — | 13.5 | 50.1 | 0.9 | 0.2 | 0.1 | — | 0.6 |
| | | | | 1.65 | 4 | 34.3 | — | 13.5 | 49.9 | 0.9 | 0.2 | 0.1 | 0.1 | 0.5 |
| | | | | | 5 | 27.5 | — | 14.2 | 55.9 | 1.0 | 0.3 | 0.1 | 0.1 | 0.6 |
| | | | | | 6 | 34.3 | — | 13.6 | 49.9 | 0.9 | 0.2 | 0.1 | 0.1 | 0.5 |
| | | | | 3.3 | 7 | 33.8 | — | 13.4 | 50.3 | 0.9 | 0.2 | 0.1 | 0.4 | 0.4 |
| | | | | | 8 | 32.2 | — | 13.7 | 51.6 | 0.8 | 0.2 | 0.1 | 0.6 | 0.4 |
| | | | | | 9 | 33.9 | — | 13.5 | 50.0 | 0.8 | 0.2 | 0.1 | 0.8 | 0.4 |
| Feed: | | | | | 3 | 25.4 | — | 13.5 | 38.1 | — | 0.1 | 1.6 | 21.1 | — |

What is claimed is:

1. In a method for cosynthesis of phenol and acetone by acid-catalyzed decomposition over a catalyst, the improvement comprising reacting cumene hydroperoxide over an acidic smectite clay catalyst at a temperature of about 20° C. to 150° C. and a pressure of from zero to 1000 psig.

2. The method of claim 1 wherein the smectite clay is an acidic montmorillonite silica-alumina clay possessing a stucture represented by:

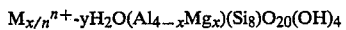

$$M_{x/n}{}^{n+} \cdot yH_2O(Al_{4-x}Mg_x)(Si_8)O_{20}(OH)_4$$

where M represents the interlamellar balancing cations from the group consisting of sodium or lithium and x, y and n are integers, and the acidities of said clay are in the range of 3 to 15 mg KOH/gm, or greater.

3. The method of claim 1 wherein the smectite clays are in a form from the group consisting of powders, granular forms or extruded forms.

4. The method of claim 1 wherein phenol/acetone are produced continuously and the feed liquid hourly space velocity (LHSV) is between 1 and 60 or greater.

5. The method of claim 1 wherein the temperature is between 40° and 120° C.

6. The method of claim 2 wherein the acidic clay has an acidity in the range of 3 to 15 mg KOH/gm, titrated to a phenolphthalein end point.

7. The method of claim 3 wherein the surface area of the catalyst is from 30 m²/g to 1000 m²/g.

8. The method of claim 7 wherein the surface area of the catalyst is from 200 m²/g to 1000 m²/g.

9. The method of claim 2 further comprising limiting the moisture content of the catalyst by heating to about 220° F.

10. The method of claim 2 wherein the operating pressure is from zero to 1000 psig.

11. The method of claim 2 wherein the operating pressure is from 100 psig to 400 psig.

12. The method of claim 2 wherein the cumene hydroperoxide feedstock is at least about 80% pure.

13. The method of claim 2 wherein the cumene hydroperoxide is diluted.

14. The method of claim 13 wherein the diluent is selected from the group consisting of acetone, a mix of acetone or cumene and phenol.

15. The method of claim 2 wherein the hydroperoxide conversions are 98 mole% or better.

16. The method of claim 2 wherein the total liquid hourly space velocity is one to 10, under mild conditions.

17. The method of claim 2 wherein there is no significant quantity of mesityl oxide by product formed.

* * * * *